(12) United States Patent
Goetz

(10) Patent No.: US 7,853,323 B2
(45) Date of Patent: Dec. 14, 2010

(54) SELECTION OF NEUROSTIMULATOR PARAMETER CONFIGURATIONS USING NEURAL NETWORKS

(75) Inventor: Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 484 days.

(21) Appl. No.: 11/824,219

(22) Filed: Jun. 29, 2007

(65) Prior Publication Data
US 2007/0276441 A1 Nov. 29, 2007

Related U.S. Application Data

(63) Continuation of application No. 10/767,922, filed on Jan. 29, 2004, now Pat. No. 7,252,090.

(60) Provisional application No. 60/503,206, filed on Sep. 15, 2003.

(51) Int. Cl.
*A61N 1/36* (2006.01)

(52) U.S. Cl. .................. 607/2; 607/45; 607/5; 607/7; 607/27; 607/46; 607/60; 607/116; 607/117; 607/546; 706/15; 706/16; 706/18; 706/19; 706/26; 706/34; 706/35; 706/44; 706/48; 128/925

(58) Field of Classification Search .................. 607/2, 607/5, 7, 27, 45–46, 55–57, 60, 116, 117; 600/546; 128/925; 706/48, 15–16, 18, 19, 706/26, 34, 35, 44

See application file for complete search history.

(56) References Cited

U.S. PATENT DOCUMENTS

| | | | |
|---|---|---|---|
| 4,872,122 | A | 10/1989 | Altschuler et al. |
| 4,895,574 | A | 1/1990 | Rosenberg |
| 5,005,143 | A | 4/1991 | Altschuler et al. |

(Continued)

FOREIGN PATENT DOCUMENTS

EP 0 653 224 A2 5/1995

(Continued)

OTHER PUBLICATIONS

The International Search Report from corresponding PCT Application Serial No. PCT/US2004/029850 mailed Nov. 30, 2004 (3 pages).

(Continued)

*Primary Examiner*—Carl H Layno
*Assistant Examiner*—Deborah Malamud
(74) *Attorney, Agent, or Firm*—Shumaker & Sieffert, P.A.

(57) ABSTRACT

In general, the invention is directed to a technique for selection of parameter configurations for a neurostimulator using neural networks. The technique may be employed by a programming device to allow a clinician to select parameter configurations, and then program an implantable neurostimulator to deliver therapy using the selected parameter configurations. The parameter configurations may include one or more of a variety of parameters, such as electrode configurations defining electrode combinations and polarities for an electrode set implanted in a patient. The electrode set may be carried by one or more implanted leads that are electrically coupled to the neurostimulator. In operation, the programming device executes a parameter configuration search algorithm to guide the clinician in the selection of parameter configurations. The search algorithm relies on a neural network that identifies potential optimum parameter configurations.

40 Claims, 5 Drawing Sheets

U.S. PATENT DOCUMENTS

| | | |
|---|---|---|
| 5,240,009 A | 8/1993 | Williams |
| 5,280,792 A | 1/1994 | Leong et al. |
| 5,358,513 A | 10/1994 | Powell et al. |
| 5,383,910 A | 1/1995 | den Dulk |
| 5,443,486 A | 8/1995 | Hrdlicka et al. |
| 5,522,863 A | 6/1996 | Spano et al. |
| 5,626,140 A | 5/1997 | Feldman et al. |
| 5,645,069 A | 7/1997 | Lee |
| 5,673,367 A | 9/1997 | Buckley |
| 5,702,429 A | 12/1997 | King |
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |
| 5,782,885 A | 7/1998 | Andersson |
| 5,788,645 A | 8/1998 | Swanson et al. |
| 5,810,014 A | 9/1998 | Davis et al. |
| 5,867,386 A | 2/1999 | Hoffberg et al. |
| 5,871,507 A | 2/1999 | Obel et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,995,868 A | 11/1999 | Dorfmeister et al. |
| 5,999,854 A | 12/1999 | Deno et al. |
| 6,081,750 A | 6/2000 | Hoffberg et al. |
| 6,108,578 A | 8/2000 | Bardy et al. |
| 6,129,745 A | 10/2000 | Sun et al. |
| 6,171,239 B1 | 1/2001 | Humphrey |
| 6,192,273 B1 | 2/2001 | Igel et al. |
| 6,263,230 B1 | 7/2001 | Haynor et al. |
| 6,269,267 B1 | 7/2001 | Bardy et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,658,287 B1 | 12/2003 | Litt et al. |
| 6,659,968 B1 | 12/2003 | McClure |
| 6,662,051 B1 | 12/2003 | Eraker et al. |
| 6,697,672 B2 | 2/2004 | Andersson |
| 6,704,595 B2 | 3/2004 | Bardy |
| 7,123,961 B1 | 10/2006 | Kroll et al. |
| 2002/0016699 A1 | 2/2002 | Hoggart et al. |
| 2002/0038294 A1 | 3/2002 | Matsugu |
| 2002/0045804 A1 | 4/2002 | Christopher et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0095189 A1 | 7/2002 | Andersson |
| 2002/0099303 A1 | 7/2002 | Bardy |
| 2002/0103512 A1 | 8/2002 | Echauz et al. |
| 2002/0106709 A1 | 8/2002 | Potts et al. |
| 2002/0123673 A1 | 9/2002 | Webb et al. |
| 2002/0133198 A1 | 9/2002 | Kramer et al. |
| 2002/0138013 A1 | 9/2002 | Guerrero et al. |
| 2002/0143262 A1 | 10/2002 | Bardy |
| 2002/0151992 A1 | 10/2002 | Hoffberg et al. |
| 2002/0169367 A1 | 11/2002 | Bardy |
| 2002/0169483 A1 | 11/2002 | Henry et al. |
| 2002/0173727 A1 | 11/2002 | Bardy |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0158587 A1 | 8/2003 | Esteller et al. |
| 2003/0195569 A1 | 10/2003 | Swerdlow et al. |
| 2003/0216654 A1 | 11/2003 | Xu et al. |
| 2004/0103001 A1 | 5/2004 | Mazar et al. |
| 2004/0129271 A1 | 7/2004 | Hickle |
| 2004/0158298 A1 | 8/2004 | Gliner et al. |

FOREIGN PATENT DOCUMENTS

| | | |
|---|---|---|
| EP | 0 653 224 B1 | 5/1995 |
| EP | 0 541 338 | 9/1996 |
| EP | 0 756 877 | 2/1997 |
| EP | 0 796 636 | 9/1997 |
| EP | 0 684 858 | 4/1998 |
| EP | 0 848 965 A2 | 6/1998 |
| EP | 0 882 469 | 12/1998 |
| EP | 1 192 971 | 4/2002 |
| EP | 0 848 965 B1 | 8/2003 |
| EP | 0 653 224 | 1/2004 |
| WO | WO 00/10455 | 3/2000 |
| WO | WO 01/17419 | 3/2001 |
| WO | WO 01/43823 | 6/2001 |
| WO | WO 01/56467 | 8/2001 |
| WO | WO 01/60445 | 8/2001 |
| WO | WO 01/82995 | 11/2001 |
| WO | WO 02/02622 | 1/2002 |
| WO | WO 02/15777 | 2/2002 |
| WO | WO 03/033070 | 4/2003 |
| WO | WO 03/037231 | 5/2003 |
| WO | WO 03/094721 | 11/2003 |
| WO | WO 2004/031919 | 4/2004 |

OTHER PUBLICATIONS

The International Preliminary Report on Patentability from corresponding PCT Application Serial No. PCT/US2004/029850 mailed Sep. 21, 2005 (9 pages).

SELECTION OF NEUROSTIMULATOR PARAMETER CONFIGURATIONS USING NEURAL NETWORKS

This application is a continuation of U.S. application Ser. No. 10/767,922, now issued as U.S. Pat. No. 7,252,090, filed Jan. 29, 2004, which claims the benefit of U.S. provisional application Ser. No. 60/503,206, filed Sep. 15, 2003. The entire content of both applications is incorporated herein by reference.

TECHNICAL FIELD

The invention relates to neurostimulation therapy and, more particularly, to techniques for selection of parameter configurations for an implantable neurostimulator.

BACKGROUND

Implantable medical devices are used to deliver neurostimulation therapy to patients to treat a variety of symptoms or conditions such as chronic pain, tremor, Parkinson's disease, epilepsy, incontinence, sexual dysfunction, or gastroparesis. The implantable medical device delivers neurostimulation therapy via one or more leads that include electrodes located proximate to the spinal cord, pelvic nerves, sacrum, or stomach, or within the brain of a patient. In general, the implantable medical device delivers neurostimulation therapy in the form of electrical pulses.

A clinician selects values for a number of programmable parameters in order to define a parameter configuration for the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient, and duration for which the stimulation energy is delivered. In addition, the clinician also selects particular electrodes within an electrode set to be used to deliver the pulses, and the polarities of the selected electrodes. The electrode combination and polarities may be referred to as an electrode configuration. Hence, a parameter configuration may involve a variety of parameters including electrode configuration, amplitude, pulse width, pulse rate, and duration.

The process of selecting parameter configurations can be time consuming, and may require a great deal of trial and error before an optimum electrode configuration is discovered. The optimum parameter configuration may be better than other configurations in balancing clinical results and side effects experienced by the patient. This balance represents overall efficacy of a parameter configuration. The process for selecting parameter configurations can be difficult due to the combinatorial possibilities of parameters, the complexity of the underlying biophysics, and subjective and possibly inconsistent feedback from the patient concerning observed efficacy for a given parameter configuration.

SUMMARY

In general, the invention is directed to a technique for selection of parameter configurations for a neurostimulator using neural networks. The technique may be employed by a programming device to allow a clinician to select parameter configurations, and then program an implantable neurostimulator to deliver therapy using the selected parameter configurations.

A parameter configuration may define one or more parameters for delivery of neurostimulation, such as electrode configuration, amplitude, pulse width, pulse rate, or duration. For example, the parameter configurations may define electrode configurations that specify electrode combinations and polarities for an electrode set implanted in a patient. The electrode set may be carried by one or more implanted leads that are electrically coupled to the neurostimulator. In some embodiments, the parameter configurations may further define one or more parameters such as amplitudes, pulse widths, pulse rates, and durations of stimulation energy delivered by electrodes in the electrode configuration.

In operation, the programming device executes a parameter configuration search algorithm to guide the clinician in the selection of parameter configurations. The search algorithm relies on a neural network that identifies potential optimum parameter configurations, such as electrode configurations within an electrode set. The neural network is trained to classify optimum parameter configurations based on observed example configurations within a programming session.

The neural network structure can be trained, from a set of existing parameter configuration data, and then learn in the course of evaluating new parameter configurations. In particular, the neural network may be updated based on new observations obtained for parameter configurations during the search. With the aid of the neural network, a programming device provides a clinician with suggestions of which configurations are most likely to be efficacious given observations already obtained during the selection process.

In general, efficacy refers to the balance between therapeutic benefit and undesirable side effects. As examples, efficacy can be observed by verbal feedback from the patient concerning therapeutic benefit and side effects, marking of a pain/parasthesia map, objective measurement using pain rating scales, quantification of side effects, a combination of the forgoing, or other observation techniques.

In one embodiment, the invention provides a method comprising selecting a first parameter configuration for a neurostimulator, observing efficacy of the first parameter configuration, and selecting a second parameter configuration for the neurostimulator from a set of additional parameter configurations identified by a neural network.

In another embodiment, the invention provides a computer-readable medium comprising instructions to cause a processor to select a first parameter configuration for a neurostimulator, observe efficacy of the first parameter configuration, and select a second parameter configuration for the neurostimulator from a set of additional parameter configurations identified by a neural network.

In a further embodiment, the invention provides a device comprising a processor programmed to select a first parameter configuration for a neurostimulator, observe efficacy of the first parameter configuration, and select a second parameter configuration for the neurostimulator from a set of additional parameter configurations identified by a neural network.

The invention may provide a number of advantages. For example, the invention may allow a clinician to more quickly identify desirable parameter configurations such as electrode combinations, reducing the overall amount of time the clinician spends programming neurostimulation therapy for a patient. In contrast to random or idiosyncratic search techniques, a technique based on neural networks is capable of learning from the evaluation of earlier parameter configurations, and developing a network structure that is more likely to lead to an optimum configuration. In general, the invention can reduce the length of a programming session for the clinician and the patient, and support selection of optimum electrode configurations to achieve overall efficacy. In addition, with the invention, it may be possible to identify optimal or near optimal parameter configurations that otherwise might not be identified by the clinician.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
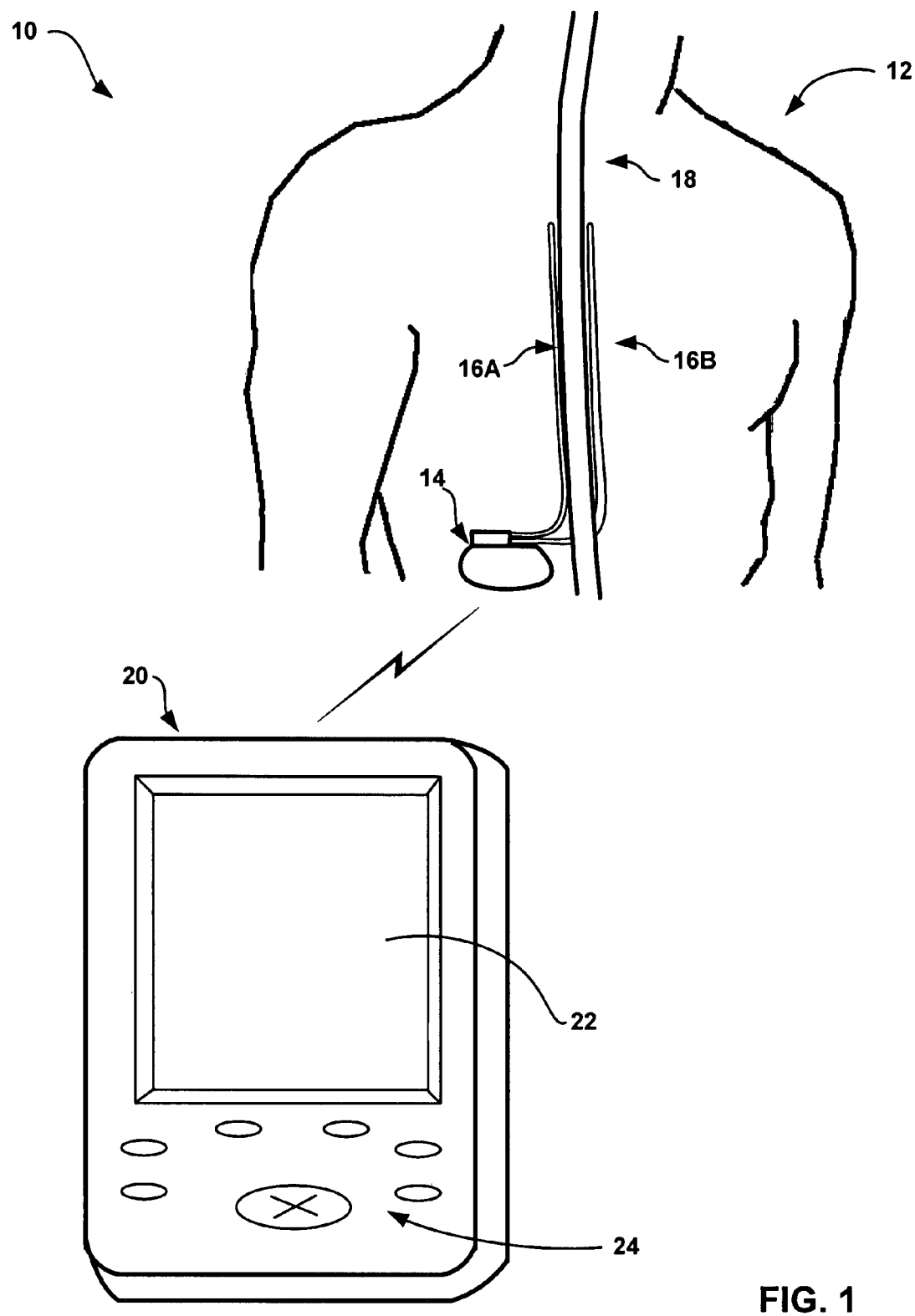
FIG. 1 is a diagram illustrating a system for programming and delivering neurostimulation therapy.

FIG. 1 is a diagram illustrating an example system 10 for programming neurostimulation therapy for and delivering neurostimulation therapy to a patient 12. System 10 includes an implantable medical device (IMD) 14 that delivers neurostimulation therapy to patient 12. IMD 14 may be an implantable pulse generator, and may deliver neurostimulation therapy to patient 12 in the form of electrical pulses. System 10 makes use of neural network structures for selection of parameter configurations.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown), sacrum (not shown) or stomach (not shown), and IMD 14 may deliver neurostimulation therapy to treat incontinence, sexual dysfunction, or gastroparesis.

IMD 14 delivers neurostimulation therapy to patient 12 according to one or more neurostimulation therapy programs. A neurostimulation therapy program may include values for a number of parameters, and the parameter values define a parameter configuration for delivery of the neurostimulation therapy according to that program. In embodiments where IMD 14 delivers neurostimulation therapy in the form of electrical pulses, the parameters may include pulse voltage or current amplitudes, pulse widths, pulse rates, durations and the like. Further, each of leads 16 includes electrodes (not shown in FIG. 1), and the parameters for a program may include information identifying which electrodes have been selected for delivery of pulses according to the program, and the polarities of the selected electrodes. Hence, a parameter configuration may involve one or more of a variety of parameters including electrode configuration, amplitude, pulse width, pulse rate, and duration. Although the invention may be applicable to neurostimulation parameter configuration in general, including configuration of parameters such as amplitude, pulse width, pulse rate, duration and electrode configuration, the invention generally will be described for purposes of illustration in the context of determining an electrode configuration.

A selected subset of the electrodes located on leads 16 and the polarities of the electrodes of the subset collectively define an "electrode configuration." The electrodes may be arranged in a standard inline lead configuration, or as a surgical paddle lead, grid, or other format. Electrode configurations refer to combinations of single or multiple cathode electrodes and single or multiple anode electrodes. Stimulation current flows between the cathodes and anodes for delivery of neurostimulation therapy. Hence, the polarities of the individual electrodes are another feature of the electrode configuration. Electrodes forming part of an electrode configuration may reside together on a single lead or on different leads.

System 10 also includes a programmer 20. Programmer 20 may, as shown in FIG. 1, be a handheld computing device. Programmer 20 includes a display 22, such as a liquid crystal display (LCD) or light emitting diode (LED) display, to display information to a user. Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions.

A clinician (not shown) or other user may use programmer 20 to program neurostimulation therapy for patient 12. In particular, the clinician may use programmer 20 to create neurostimulation therapy programs. In some embodiments, programmer 20 may be used by the patient, e.g., over an extended trial screening process. As part of the program creation process, programmer 20 allows the clinician to identify parameter configurations that enable IMD 14 to deliver neurostimulation therapy that is desirable in terms of, for example, symptom relief, coverage area relative to symptom area, and side effects. Programmer 20 may also allow the clinician to identify parameter configurations that enable IMD 14 to deliver effective neurostimulation therapy with desirable device performance characteristics, e.g., low battery consumption. In addition, techniques as described herein may used to optimize therapy over the course of use of a chronically implanted IMD, e.g., by interaction between patient 12 and a patient programmer to record efficacy observations over time. In this case, a programmer carried by the patient may incorporate some or all of the functionality attributed to programmer 20 as described herein, including functionality designed to assist in identification of parameter configurations using neural networks.

Programmer 20 controls IMD 14 to test parameter configurations in order to allow a clinician to identify desirable parameter configurations in an efficient manner. As will be described in greater detail below, in some embodiments, programmer 20 selects parameter configurations to test based on an electrode configuration search algorithm, as described herein. In particular, according to such an algorithm, programmer 20 may first control IMD 14 to test one or more electrodes to identify a first electrode configuration, and then test other electrode configurations based on guidance built into the search algorithm.

Other neurostimulation parameters such as amplitude, pulse width, pulse rate, and duration also may be evaluated with the electrode configuration. For example, various parameters may be observed simultaneously with observation of each electrode configuration. Alternatively, once a smaller set of electrode configurations has been identified as providing efficacy for a given baseline set of amplitude, pulse width and pulse rate, then different amplitude, pulse width and pulse rate parameters may be iteratively observed for that smaller set of electrode configurations. Duration of the delivery of neurostimulation energy also may be observed. In this manner, amplitude, pulse width, and pulse rate parameters need not be evaluated for every electrode configuration, and especially those electrode configurations that do not present a high probability of efficacy as inferred from the neural network structure.

By controlling IMD 14 to test parameter configurations in an intelligent manner, programmer 20 allows the clinician to more quickly identify desirable parameter configurations, reducing the overall amount of time the clinician spends programming neurostimulation therapy for patient 12. For example, in contrast to existing neurostimulation programming systems that present electrode configurations in a random order or idiosyncratic search methodologies employed by clinicians, programmer 20 may select electrode configurations to test in a way that is more likely to enable desirable configurations to be selected earlier in the search. Consequently, the clinician may be able to end the search before all potential electrode combinations have been tested if one or more desirable configurations have already been identified, saving the amount clinician and patient time required to achieve an efficacious electrode configuration. In addition, with the invention, it may be possible to identify optimal or near optimal parameter configurations that otherwise might not be identified by the clinician.

Even if the clinician elects to test all potential electrode combinations, e.g., if the electrode set is small enough to make testing all electrode configurations practical, programmer 20 may reduce the time required to identify desirable electrode configurations by automating selection of each new configuration to test. Additionally, programmer 20 may improve the search process by collecting efficacy information for each combination tested. As will be described in greater detail below, programmer 20 may present a list of electrode configurations to the clinician, ordered according to the efficacy information, allowing the clinician to more easily identify and select desirable configurations. This list of electrode configurations may be ordered and updated according to newly observed efficacy information as additional electrode configurations are evaluated. Similar techniques may be applied for other neurostimulation parameters forming part of a parameter configuration, such as amplitude, pulse width, pulse rate, and duration.

In order to control IMD 14 to test electrode combinations, programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of parameter configurations associated with neurostimulation therapy programs. Neurostimulation therapy programs created by the clinician using programmer 20 may be transmitted to IMD 14 via telemetry, and/or may be transmitted to another programmer (not shown), e.g., a patient programmer, that is used by patient 12 to control the delivery of neurostimulation therapy by IMD 14.

Figure 2:
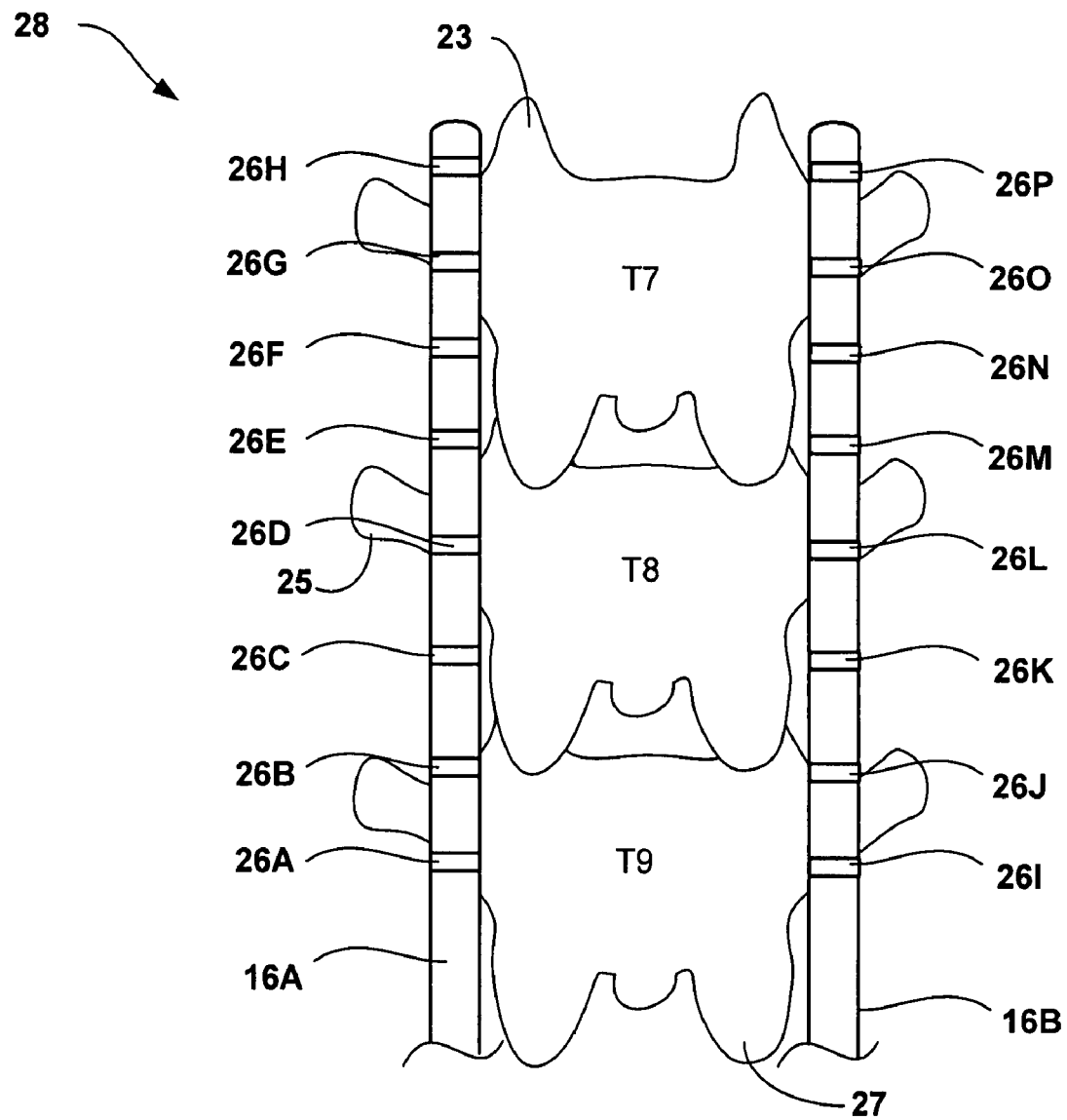
FIG. 2 is a diagram illustrating an example electrode set implanted proximate to the spine of a patient.

FIG. 2 is a block diagram illustrating an example configuration of leads 16. In the example configuration, lead 16A includes electrodes 26A-26H, and lead 16B includes electrodes 26I-26P. Hence, each lead 16 includes eight electrodes, although a lesser or greater number of electrodes are possible. Electrodes 26A-P (collectively "electrodes 26") may be ring electrodes. Electrodes 26 collectively form an electrode set 28 implanted within patient 12. As shown in FIG. 2, electrode set 28 includes eight electrodes on each of the two leads 16, which, as shown in FIG. 1, are implanted such that they are substantially parallel to each other and spinal cord 18 (FIG. 1), on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 28 may be described as a two-by-eight, side-by-side, upwardly oriented configuration. Of course, electrode set 28 is provided for purposes of example, and the invention may be applicable to other types of leads and electrode sets, including single lead electrode sets, flat paddle leads, grid arrays, and the like Such an electrode set is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20. In the example of FIG. 2, electrodes 26 are placed on opposite sides of the T7 vertebra 23, T8 vertebra 25 and T9 vertebra 27 of a human spine.

IMD 14 (FIG. 1) may deliver neurostimulation via any combination of electrodes 26. IMD 14 may independently activate each electrode 26 of set 28 to act as a cathode or anode for a configuration, and each configuration will include at least one cathode and at least one anode. In some embodiments, it is possible that an electrode configuration may include a single electrode 26 acting as the cathode, with a can of IMD 14, i.e., the IMD housing, acting as the anode for the configuration.

In an electrode configuration, electrons flow from one or more electrodes acting as anodes for the configuration to one or more electrodes acting as cathodes for the configuration. The current between anodes and cathodes stimulates neurons between and proximate to the anodes and cathodes. Generally speaking, an electrode configuration enables desirable neurostimulation therapy when current is delivered in a direction and with an intensity sufficient to stimulate specific neurons or a sufficient number of specific neurons to alleviate a symptom without causing unacceptable side effects. Further, an electrode configuration enables desirable neurostimulation therapy when the symptom is alleviated without resorting to undesirably high pulse amplitudes.

As mentioned above, programmer 20 selects individual electrodes 26 or electrode configuration to test to allow a clinician to identify desirable electrode configuration according to an electrode search algorithm. Programmer 20 may select an appropriate search algorithm based on the configuration of electrode set 28, and may select electrodes 26 or electrode configurations based on the selected search algorithm. Programmer 20 controls IMD 14 to test a selected electrode 26 or electrode combination by controlling IMD 14 to deliver neurostimulation via the selected electrode 26 or combination.

In some embodiments, programmer 20 may first control IMD 14 to test one or more of electrodes 26 individually to identify the individual electrode or electrodes 26 which will act as a first cathode. In other embodiments, programmer 20 starts with a combination of selected electrodes 26. Generally, a clinician implants leads 16 in a location such that the center of electrode set 28 is proximate to an area that the clinician believes should be stimulated in order to alleviate symptoms. Therefore, programmer 20 may test electrodes 26 as the first cathode in an order such that electrodes 26 located centrally within electrode set 28, e.g., electrodes 26D-E and 26L-M illustrated in FIG. 2, are tested before peripherally located electrodes. If the clinician's estimation of the target region is inaccurate, programmer 20 will continue to test individual electrodes 26 in such an order until one of the electrodes 26 that enables desirable neurostimulation therapy when activated as the first cathode is identified. Initially locating a first cathode provides a "coarse" optimization of electrode combinations, allowing programmer 20 and the clinician to quickly identify the general area to which neurostimulation therapy should be delivered.

Programmer 20 may then control IMD 14 to test electrode configurations that include the first cathode. The various electrode configurations may be tested with a common set of stimulation parameters, such as a common voltage or current amplitude, frequency, and pulse width. In some embodiments, a series of different stimulation parameters may be applied for each combination of electrodes to test not only the efficacy of electrode combinations, but also electrode combinations with particular stimulation parameters such as amplitude, frequency and pulse width. Hence, an electrode configuration may apply to the combination of electrodes forming part of the neurostimulation parameter configuration, and the parameters associated with delivery of neurostimulation energy via the electrodes, such as amplitude, pulse width and pulse rate, may form another part of the parameter configuration.

Programmer 20 may control IMD 14 to try different ones of electrodes 26 as the first anode in a pair with the first cathode, and may add additional anodes and/or cathodes. In accordance with an embodiment of the invention, programmer 20 controls IMD 14 to test remaining electrodes 26 as first anodes, and additional anodes or cathodes, based on electrode configurations identified by a neural network. The neural network may be employed by programmer 20 to allow a clinician to select electrode configurations, and then program IMD 14 to deliver therapy using the selected electrode configurations. The neural network structure classifies optimum electrode configurations.

The search algorithm uses the neural network structure to infer likely efficacies of possible parameter configurations, such as electrode configurations, based on the efficacies of parameter configurations already observed in the course of evaluation. The network structure can be learned from an existing set of data, or developed based on the input of a neurostimulation expert. In particular, the neural network structure may be updated based on new observations obtained for newly considered electrode configurations during the search. With the aid of the neural network, a programmer 20 provides a clinician with suggestions of electrode configurations that are likely to be efficacious given observations already obtained during the selection process. In response, the clinician may select the suggested electrode configurations next. In some cases, the selection of electrode configurations, or other parameters, may be automated in response to suggestions generated using the neural network. In other cases, the selection of the parameter configurations may require human intervention from the clinician, but be aided by the suggestions.

As an illustration, an expert, such as a neurostimulation physician, may initially develop the neural network structure based on his or her knowledge of typical relationships among different electrode configurations. As actual electrode configurations are observed, however, the causal relationships may be supplemented with actual data. The actual data may be archived and used as the basis for a development of future neural network structure.

In some embodiments, a plurality of different neural network structures may be developed and devised for specific applications, such as different types of neurostimulation therapy, different symptomatic regimes, different electrode structures and device capabilities, and so forth. Hence, for selection of an electrode configuration, the user may first select a neural network structure suitable for the present circumstances, and then use the selected network structure to guide the selection process.

Hence, the neural network structure can be used to guide an parameter configuration optimization process by selecting, as the next configuration for the clinician to try, a configuration that is more likely to yield efficacious results, e.g., in terms of symptom relief, coverage area relative to symptom area, and side effects. In this way, the number of observations that need be made to ensure a good outcome is reduced.

Figure 3:
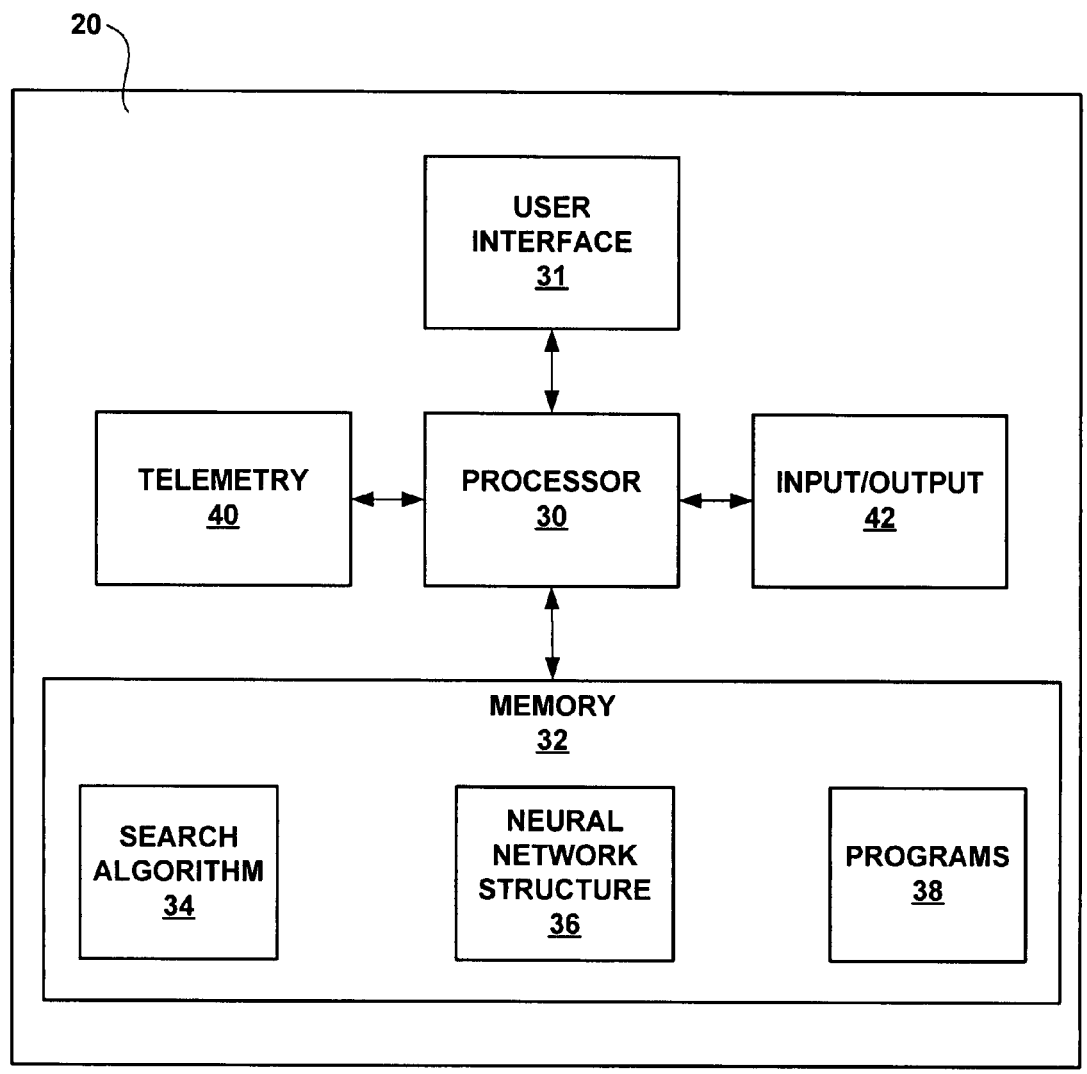
FIG. 3 is a block diagram illustrating a programming device used to identify desirable parameter configurations for neurostimulation therapy programs.

FIG. 3 is a block diagram illustrating an example configuration of programmer 20. A clinician or other user may interact with a processor 30 via a user interface 31 in order to identify and select electrode configurations as described herein. User interface 31 may include display 22 and keypad 24 (FIG. 1), and may also include a touch screen or peripheral pointing devices as described above. Processor 30 may also provide a graphical user interface (GUI) via user interface 31 to facilitate interaction with a clinician, technician, or other medical personnel. Processor 30 may include a microprocessor, a controller, a DSP, an ASIC, an FPGA, discrete logic circuitry, or the like.

Clinician programmer 20 also includes a memory 32. Memory 32 may include program instructions that, when executed by processor 30, cause clinician programmer 20 to perform the functions ascribed to clinician programmer 20 herein. For example, processor may execute a parameter configuration search algorithm 34 stored within memory 32. In particular, processor 30 may execute an electrode configuration search algorithm to select individual electrodes 26 or electrode combinations to test to allow the clinician to identify desirable electrode combinations. Search algorithm 34 executes based on the content of a neural network structure 36, which classifies electrode configurations within electrode set 28 according to predicted efficacy.

Hence, programmer 20 provides interactive guidance to a clinician during the process of optimizing implantable device parameters. In particular, programmer 20 guides the clinician by suggesting the electrode configurations that are most likely to be efficacious given the results of tests already performed during the source of an evaluation session. This is accomplished by training the neural network to classify optimum configurations based on observed examples within a session. Inputs to this neural network would include efficacy ratings from one or more electrode configurations previously tried in that session. The output is the best guess of the neural network as to the optimum configuration. This guess then becomes the suggestion for the next electrode configuration to be tried by the clinician, and rated by the clinician, patient, or both.

The neural network can be trained using methods such as back-propagation from a large, existing set of example records containing data based on previous observations. An input node may be included in the neural network for each unique input configuration. The neural network provides an output layer, either a single node or a series of nodes, that encodes the possible optimum configurations. One or more hidden layers may be included in the neural network, as necessary.

As will be described in greater detail below, processor 30 collects information relating to tested parameter configurations, such as electrode configurations, and stores the information in memory 32 for later retrieval and review by the clinician to facilitate identification of desirable parameter configurations. Neurostimulation therapy programs 38 created by the clinician may be stored in memory 32, and information identifying electrode configurations selected by the clinician to be utilized for one of programs 38 may be stored as part of the program within memory 32. Memory 32 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 30 controls IMD 14 to test selected individual electrodes 26 or electrode combinations, by controlling IMD 14 to deliver neurostimulation therapy to patient 12 via the selected individual electrodes 26 or electrode combinations via a telemetry circuit 40. Processor 30 may transmit programs 38 created by the clinician to IMD 14 via telemetry circuit 40, or to another programmer used by the patient to control delivery of neurostimulation therapy via input/output circuitry 42. I/O circuitry 42 may include transceivers for wireless communication, appropriate ports for wired communication or communication via removable electrical media, or appropriate drives for communication via removable magnetic or optical media.

Figure 4:
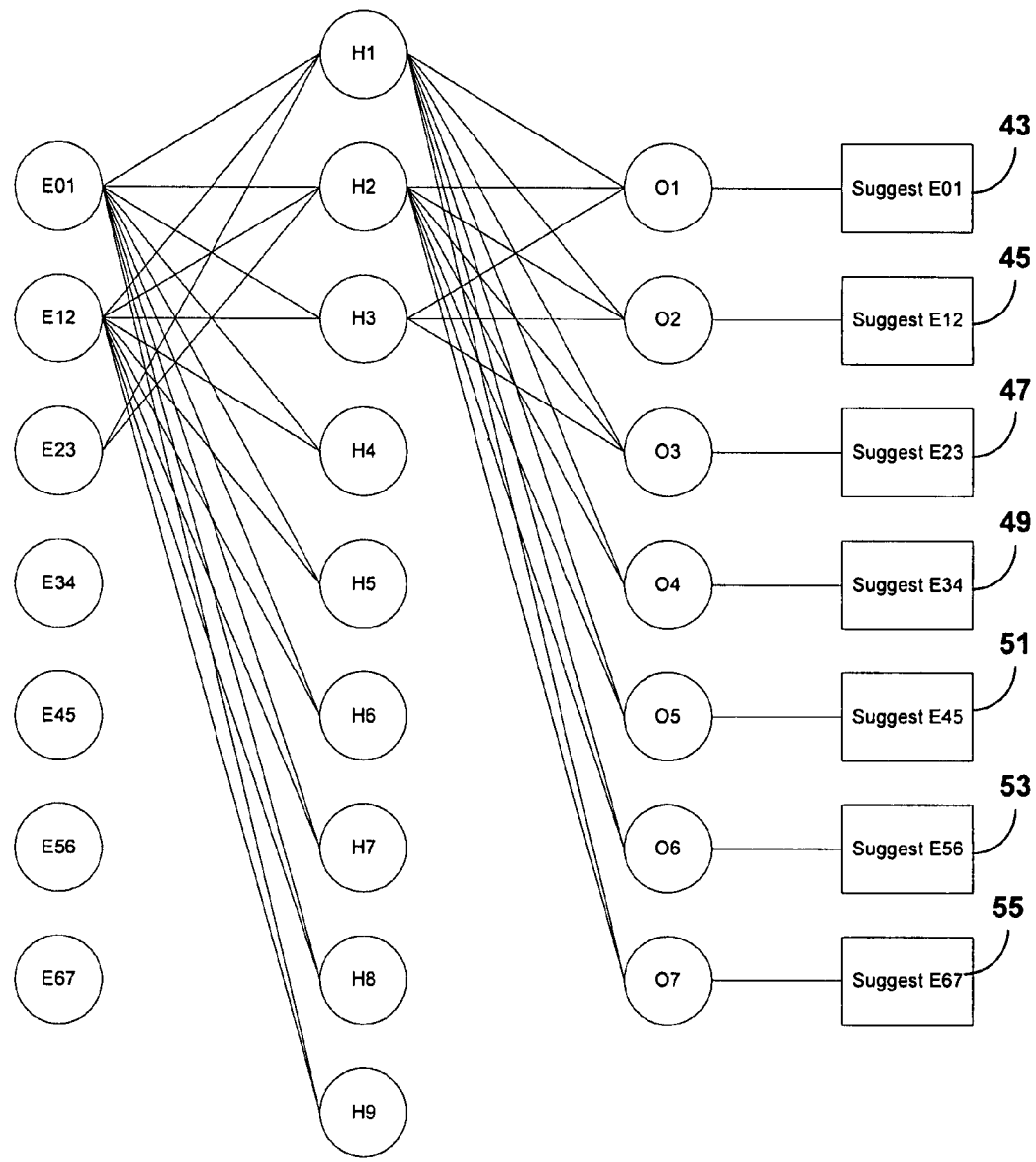
FIG. 4 is a diagram illustrating the structure of a neural network configured to identify optimal parameter configurations.

FIG. 4 is a diagram illustrating the structure of a neural network configured to identify optimal electrode configurations. As shown in FIG. 4, the neural network is characterized by nodes, layers and interconnections. As a specific example, consider the problem of selecting the optimum electrode bipole on a 1×8 stimulation lead. Inputs for this problem include the efficacy ratings for each possible bipole combination E01, E12, . . . , E67, where E01 represents a combination of electrode 0 and electrode 1 on the lead, E12 represents a combination of electrode 1 and electrode 2 on the lead, and so forth.

In the example of FIG. 4, the polarity of the electrodes, i.e., relative placement of anode and cathode on the bipole pair, is no considered, but the system 10 can be readily adapted to support polarity determinations. For this example, system 10 singly encodes (one configuration per node) the output possibilities. A single hidden layer is included with 9 nodes, though this may not be the optimum size or number of layers in some applications. In FIG. 4, only a subset of interconnection weights are shown. In practice, however, the neural network may be fully connected, with every input node connecting to every hidden node, and every hidden node connecting to every output node. In FIG. 4, the "E" nodes (E01, E12, E23, E34, E45, E56, E67) represent input nodes, the "H" nodes (H1, H2, H3, H4, H5, H6, H7, H8, H9) represent hidden nodes, and the "O" nodes (O1, O2, O3, O4, O5, O6, O7) represent output nodes that yield suggested electrode configurations 43, 45, 47, 49, 51, 52, 55.

Using the neural network structure, programmer 20 provides suggestions on which parameter configurations are most likely to be efficacious given the interconnection weights among the input nodes, hidden nodes and output nodes in the neural network. The interconnection weights may be initially learned, but then modified and updated based on results of efficacy observation tests performed during the course of an evaluation with a clinician or other user. In this manner, the neural network can be used to guide the clinician to a set of optimum parameter configurations for evaluation, reducing the number of observations that need be made to ensure a good outcome. In other words, the neural network may permit the clinician to avoid a number of electrode configurations that, based on previous experience, are unlikely to yield efficacious results. Rather, the interconnection of particular nodes with interconnection weights determined from past observations directs the clinician to electrode configurations that are more likely to produce optimum efficacy results.

Figure 5:
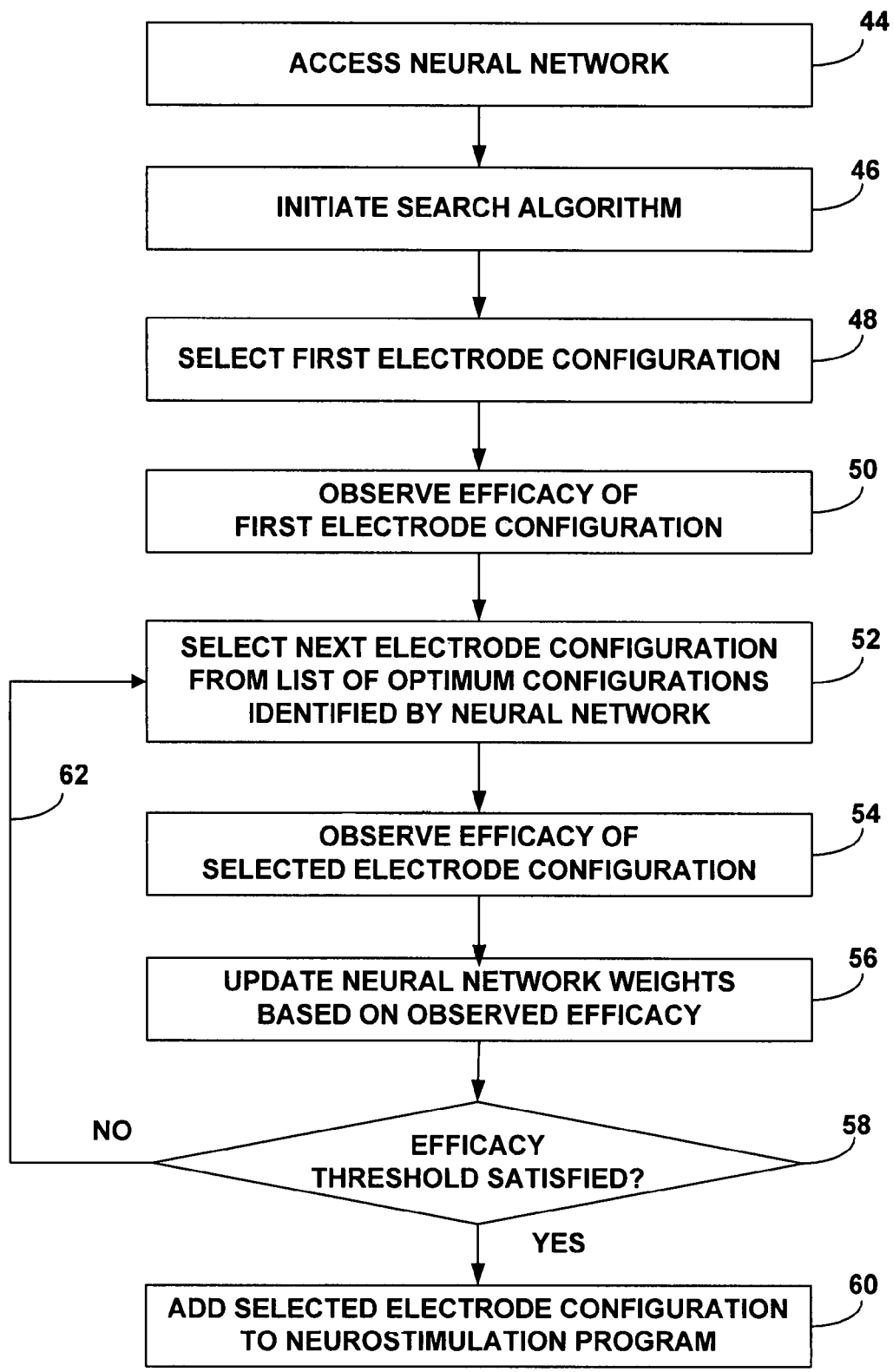
FIG. 5 is a flow diagram illustrating a search algorithm that is executable by a programmer to select parameter configurations using a neural network.

FIG. 5 is a flow diagram illustrating a search algorithm that is executable by a programmer to select electrode configurations. As shown in FIG. 5, the algorithm involves accessing the neural network (44), initiating the search algorithm (46), selecting a first electrode configuration (48), and observing the efficacy of the first electrode configuration (50). The efficacy may be rated positively in terms of pain relief or other therapeutic benefit, and negatively in terms of side effects of the therapy. The search capability can be implemented as a feature in an implantable device programmer 20.

Following the programming of a configuration of parameters, the programmer 20 may prompt for a rating of the efficacy of that configuration. The efficacy rating can be solicited from the patient by the clinician, or entered directly by the patient. In general, efficacy refers to the balance between therapeutic benefit and undesirable side effects. As examples, efficacy ratings can be obtained by verbal feedback from the patient concerning therapeutic benefit and side effects, marking of a pain/parasthesia map, objective measurement using pain rating scales, quantification of side effects, a combination of the forgoing, or other observation techniques.

The programmer 20 then uses this rating with the network model appropriate for the therapy and device type to infer the best next step. This step may then be suggested to the clinician by the programmer interface. Based on the observed efficacy and a list of optimum configurations identified by the neural network, the next electrode configuration is selected (52), either automatically or manually by the clinician.

The algorithm then involves observing efficacy of that newly selected electrode configuration (54) and updating the neural network weights or interconnections to reflect the observed efficacy (56). If an applicable efficacy threshold is satisfied (58), the algorithm may terminate and add the selected electrode configuration to a stored neurostimulation program or create a new neurostimulation program (60). If the threshold is not satisfied, the process may repeat iteratively (62) until the threshold is satisfied or the clinician elects to manually terminate the algorithm.

If the clinician stops the search before all possible combinations of electrodes 26 have been tested, programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, programmer 20 may allow clinician to spend less time searching for desirable electrode combinations in a subsequent programming session. Specifically, the programs created using the bracket combinations may enable desirable neurostimulation therapy similar to that provided in a program created with the most recently tested combination, and may be provided to patient 12 so that patient 12 can experiment with the bracket programs outside of the clinic.

As described herein, programmer 20 controls IMD 14 to test electrode configurations combination by controlling IMD 14 to deliver neurostimulation therapy via combinations of electrodes. In addition, programmer 20 may be configured to facilitate a search for other optimum therapy parameters, thereby forming a parameter configuration. For example, the clinician or programmer 20 may select desired starting points for pulse amplitude, rate and pulse width for each electrode configuration and programmer 20 may ramp the amplitude from the starting point at a first rate of amplitude increase using similar neural network techniques. Programmer 20 may increase the amplitude in, for example, a linear or stepwise fashion. In some embodiments, the clinician or patient 12 may control the rate of amplitude increase. The clinician or patient 12 stops the ramping of the amplitude when the stimulation causes discomfort, or other undesirable side effects.

Programmer 20 may reduce the amplitude at the time the ramp is stopped by some amount, e.g., a percentage, and ramps the amplitude again in order to allow the clinician and/or patient 12 to identify the amplitude that provides the best neurostimulation therapy. This second time, programmer 20 may ramp the amplitude at a slower rate of amplitude increase in order to facilitate identification of the point where best neurostimulation is achieved. Again, in some embodiments, the clinician or patient 12 may control the amplitude.

Programmer 20 stores the amplitude at the time when the best neurostimulation therapy is indicated by the clinician and/or patient 12, and rating information for the electrode combination. The clinician and/or patient 12 may provide efficacy rating information, e.g., a numerical value for one or more metrics for rating the combination, which relates to the efficacy enabled by the combination or the side effects resulting from use of the combination, or both.

The clinician may use rating information and/or the amplitude values stored for each tested combination to identify desirable electrode configurations. The configurations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Various embodiments of the invention have been described. However, one skilled in the art will appreciate that various additions and modifications can be made to these embodiments without departing from the scope of the invention. The invention may be generally applicable to any programming optimization problem in which the feedback from a configuration is available relatively quickly and within the context of the clinical programming environment. This includes the stimulation therapies for pain and movement disorders and may include other stimulation-based therapies as well.

For example, although programmer 20 has been described herein as a hand-held computing device, programmer 20 may take the form of any type of computing device, such as a laptop or desktop computer, may access resources, such as memory 54, via a computer network, such as a LAN, WAN, or the World Wide Web. Further, programmer 20 may include a plurality of computing devices, which may communicate to provide the functionality ascribed to programmer 20 herein via a computer network.

Although described herein as associated with and interacting with a clinician, i.e., a clinician programmer, programmer 20 may, be associated with patient 12, i.e., a patient programmer. In some embodiments, patient 12 may simply interact with programmer 20 in place of the clinician for some or all of the electrode combination identification process. In other embodiments, patient 12 may perform parts of the configuration identification process without being supervised by the clinician, e.g., away from the clinic, using a patient programmer. These and other embodiments are within the scope of the following claims.

The invention claimed is:

1. A method comprising:
receiving an indication of observed efficacy of stimulation delivered by a neurostimulator according to a first stimulation parameter configuration;
modifying a neural network based on the observed efficacy of the stimulation delivered according to the first stimulation parameter configuration, wherein the neural network comprises a plurality of interconnected nodes; and
identifying a second stimulation parameter configuration based on an output of the modified neural network.

2. The method of claim 1, wherein the parameter configurations include electrode configurations, each of the electrode configurations defining a combination of two or more electrodes for delivery of neurostimulation energy.

3. The method of claim 2, wherein each of the electrode configurations defines polarities for electrodes in the combination.

4. The method of claim 2, wherein the electrodes are carried by two or more implanted leads.

5. The method of claim 4, wherein the implanted leads are implanted proximate a portion of a spine of a patient.

6. The method of claim 1, wherein modifying the neural network includes modifying interconnection weights among the nodes in the neural network.

7. The method of claim 1, wherein the nodes in the neural network include input nodes identifying possible combinations of two or more electrodes, output nodes identifying suggested combinations of two or more electrodes, and hidden nodes interconnecting the input nodes and the output nodes with respective interconnection weights.

8. The method of claim 1, further comprising iteratively identifying a plurality of additional stimulation parameter configurations, each of the stimulation parameter configurations identified based on an output of the neural network as modified based on observed efficacy of stimulation delivered by the neurostimulation according to a preceding one of the plurality of stimulation parameter configurations.

9. The method of claim 8, further comprising terminating the iterative identification of additional stimulation parameter configurations when one or more termination criteria are satisfied.

10. The method of claim 9, wherein the termination criteria include selection of one of the stimulation parameter configurations with an observed efficacy that satisfies a threshold efficacy.

11. The method of claim 9, further comprising programming the neurostimulator to employ the final stimulation parameter configuration in delivery of neurostimulation therapy.

12. The method of claim 1, wherein identifying the second stimulation parameter configuration includes suggesting the second stimulation parameter configuration to a clinician.

13. The method of claim 1, wherein identifying the second stimulation parameter configuration comprises:
presenting a list of stimulation parameter configurations that includes the second stimulation parameter configuration to a user; and
ordering the list based on the output of the modified neural network.

14. The method of claim 1, wherein receiving an indication relating to observed efficacy includes receiving user input indicating observed efficacy.

15. A non-transitory computer-readable storage medium comprising instructions to cause a processor to:
receive an indication of observed efficacy of stimulation delivered by a neurostimulator according to a first stimulation parameter configuration;
modify a neural network based on the observed efficacy of the stimulation delivered according to the first stimulation parameter configuration, wherein the neural network comprises a plurality of interconnected nodes; and
identify a second stimulation parameter configuration based on an output of the modified neural network.

16. The computer-readable storage medium of claim 15, wherein the parameter configurations include electrode configurations, each of the electrode configurations defining a combination of two or more electrodes for delivery of neurostimulation energy.

17. The computer-readable storage medium of claim 16, wherein each of the electrode configurations defines polarities for electrodes in the combination.

18. The computer-readable storage medium of claim 16, wherein the electrodes are carried by two or more implanted leads.

19. The computer-readable storage medium of claim 15, wherein modifying the neural network includes modifying interconnection weights among the nodes in the neural network.

20. The computer-readable storage medium of claim 15, wherein the nodes in the neural network include input nodes identifying possible combinations of two or more electrodes, output nodes identifying suggested combinations of two or more electrodes, and hidden nodes interconnecting the input nodes and the output nodes with respective interconnection weights.

21. The computer-readable storage medium of claim 15, further comprising instructions that cause a processor to iteratively identify a plurality of additional stimulation parameter configurations, each of the stimulation parameter configurations identified based on an output of the neural network as modified based on observed efficacy of stimulation delivered by the neurostimulation according to a preceding one of the plurality of stimulation parameter configurations.

22. The computer-readable storage medium of claim 21, further comprising instructions that cause a processor to terminate the iterative identification of additional stimulation parameter configurations when one or more termination criteria are satisfied.

23. The computer-readable storage medium of claim 22, wherein the termination criteria include selection of one of the stimulation parameter configurations with an observed efficacy that satisfies a threshold efficacy.

24. The computer-readable storage medium of claim 22, further comprising instructions that cause a processor to program the neurostimulator to employ the final stimulation parameter configuration in delivery of neurostimulation therapy.

25. The computer-readable storage medium of claim 15, wherein the instructions that cause a processor to identify the second stimulation parameter configuration include instructions that cause a processor to suggest the second stimulation parameter configuration to a clinician.

26. The computer-readable storage medium of claim 15, wherein the instructions that cause a processor to identify the second stimulation parameter configuration comprise instructions that cause a processor to:
present a list of stimulation parameter configurations that includes the second stimulation parameter configuration to a user; and
order the list based on the output of the modified neural network.

27. The computer-readable storage medium of claim 15, wherein the indication relating to observed efficacy includes user input relating to observed efficacy.

28. A device comprising a processor programmed to:
receive an indication of observed efficacy of stimulation delivered by a neurostimulator according to a first stimulation parameter configuration;
modify a neural network based on the observed efficacy of the stimulation delivered according to the first stimulation parameter configuration, wherein the neural network comprises a plurality of interconnected nodes; and
identify a second stimulation parameter configuration based on an output of the modified neural network.

29. The device of claim 28, wherein the parameter configurations include electrode configurations, each of the electrode configurations defining a combination of two or more electrodes for delivery of neurostimulation energy.

30. The device of claim 29, wherein each of the electrode configurations defines polarities for electrodes in the combination.

31. The device of claim 29, wherein the electrodes are carried by two or more implanted leads.

32. The device of claim 28, wherein modifying the neural network includes modifying interconnection weights among the nodes in the neural network.

33. The device of claim 28, wherein the nodes in the neural network include input nodes identifying possible combinations of two or more electrodes, output nodes identifying suggested combinations of two or more electrodes, and hidden nodes interconnecting the input nodes and the output nodes with respective interconnection weights.

34. The device of claim 28, wherein the processor is programmed to iteratively identify a plurality of additional stimulation parameter configurations, each of the stimulation parameter configurations identified based on an output of the neural network as modified based on observed efficacy of stimulation delivered by the neurostimulation according to a preceding one of the plurality of stimulation parameter configurations.

35. The device of claim 34, wherein the processor is programmed to terminate the iterative identification of additional stimulation parameter configurations when one or more termination criteria are satisfied.

36. The device of claim 35, wherein the termination criteria include selection of one of the stimulation parameter configurations with an observed efficacy that satisfies a threshold efficacy.

37. The device of claim 28, wherein the processor is programmed to suggest the second stimulation parameter configuration to a clinician.

38. The device of claim 28, wherein the processor is programmed to:
present a list of stimulation parameter configurations that includes the second stimulation parameter configuration to a user; and
order the list based on the output of the modified neural network.

39. The device of claim 28, wherein the indication relating to observed efficacy includes user input relating to observed efficacy.

40. The device of claim 28, wherein the neurostimulator is implantable, and the device comprises an external programming device that communicates with the neurostimulator when implanted within a patient.

* * * * *